United States Patent [19]

Edwards

[11] Patent Number: 5,110,996
[45] Date of Patent: May 5, 1992

[54] PRODUCTION OF VINYLIDENE FLUORIDE

[75] Inventor: Derek W. Edwards, Runcorn, Great Britain

[73] Assignee: Imperial Chemical Industries PLC, London, England

[21] Appl. No.: 259,360

[22] Filed: Oct. 17, 1988

[30] Foreign Application Priority Data

Oct. 20, 1987 [GB] United Kingdom ............... 8724561

[51] Int. Cl.$^5$ ............................................. C07C 17/02
[52] U.S. Cl. ................................................... 570/159
[58] Field of Search ........................................ 570/159

[56] References Cited

U.S. PATENT DOCUMENTS

| | | | |
|---|---|---|---|
| 2,687,440 | 8/1954 | McGrew et al. | 570/159 |
| 3,428,695 | 2/1969 | Soulen et al. | 570/159 |
| 3,446,859 | 5/1969 | Weif et al. | 570/159 |

*Primary Examiner*—Alan Siegel
*Attorney, Agent, or Firm*—Cushman, Darby & Cushman

[57] ABSTRACT

Production of vinylidene fluoride by reacting dichlorodifluoromethane with methane in a heated reactor element containing a non-metallic packing material which is stable at the operating temperatures of the process, wherein the reactor element subjects the gaseous reactants to a temperature within the range 500° C. to 1200° C. and wherein the calculated residence time for the gaseous reactants in the reaction zone is within the range of from 0.1 to 10.0 seconds.

16 Claims, 3 Drawing Sheets

PRODUCTION OF VINYLIDENE FLUORIDE

The present invention relates to a process for the production of vinylidene fluoride (VDF)(i.e. 1,1-difluoroethylene.

It is known to produce VDF on a commercial scale using a liquid phase hydrofluorination of 1,1,1-trichloroethane to form 1-chloro-1,1-difluoroethane followed by a gas phase dehydrochlorination of this product to VDF. The reaction mixture for the process therefore employs HF which is an extremely noxious and corrosive material.

It has been proposed in U.S. Pat. No. 2,687,440 to employ the less hazardous reaction mixture of methane and dichlorodifluoromethane (DCDFM) to produce, inter alia, VDF and monochlorodifluoromethane (MCDFM) as products, using a reaction temperature of 400° to 1000° C. It is specified that the proportion of VDF to MCDFM can be varied by changing variables of the process. However, the proportion of MCDFM and other reaction products from the reaction is never inconsiderable. The examples, which base their results on the recovered products only, quote optimum conversions of DCDFM of about 25–30 mole % with selectivities towards VDF formation of 60–70 mole %, giving a VDF yield of around 20%.

It is further proposed in U.S. Pat. No. 3,428,695 to considerably decrease the amount of MCDFM formed in this reaction by employing a reaction temperature of 1100° to 2000° C. and a reaction time of 3 to 50 milliseconds. A substantially equimolar ratio of DCDFM:methane is said to be suitable, although variation of the molar ratio of DCDFM:methane of from 0.5:1 to 1:5 (i.e. 1:2 to 1:5) is said to have no substantial effect on the conversions and yields. A suitable reactor for the reaction is said to be one which has an elongated tube (e.g. of graphite) through which the reaction mixture is passed to effect the desired reaction, this tube being heatable to the desired reaction temperature by, for example, electrical induction heating. The text of U.S. Pat. No. 3,428,695, however, only indicates a maximum selectivity of VDF formation of about 75 mole % at a DCDFM conversion of about 50 mole % (giving a VDF yield of about 38%), in an example employing a reaction temperature of 1385° C. and a pressure of 26 mm Hg absolute. The process exemplified in U.S. Pat. No. 3,428,695 uses apparatus with relatively poor heat transfer characteristics, and necessitates the use of high operating temperatures, therefore, by implication, a plant incorporating such a production process will probably incur relatively high running costs. Furthermore, the high temperatures employed may encourage decomposition and the formation of unwanted by-products.

We have now devised a process for the preparation of vinylidene fluoride using the reaction between methane and DCDFM which is capable of providing as good as or even higher yields of VDF in comparison to prior art processes. With the process of the invention good yields of VDF are attainable at temperatures within the range 500° C. to 1200° C. and pressures at or around atmospheric pressure. A further advantage of the present process is that high selectivities of VDF formation are achievable over a wide range of DCDFM conversions.

According to the present invention there is provided a process for preparing vinylidene fluoride (VDF) from the reaction of dichlorodifluoromethane (DCDFM) with methane which process comprises passing a gaseous flow of methane and dichlorodifluoromethane through a heated reactor element containing a non-metallic packing material which is stable at the operating temperatures of the process, wherein the reactor element subjects the gaseous reactants to a temperature within the range 500° C. to 1200° C. and wherein the calculated residence time for the gaseous reactants in the reaction zone is within the range of from 0.1 to 10.0 seconds.

In this specification:

$$\text{Conversion (\%) (based on } DCDFM) = \frac{\text{moles of } DCDFM \text{ reacted}}{\text{moles of } DCDFM \text{ fed}} \times 100$$

$$\text{Selectivity (\%) (towards } VDF) = \frac{\text{moles of } VDF \text{ formed}}{\text{moles of } DCDFM \text{ reacted}} \times 100$$

and $$\text{Yield (\%)} = \frac{\text{Conversion (\%)} \times \text{Selectivity (\%)}}{100}$$

(NB. No normalisation of molar quantities is necessary as one mole of DCDFM is resquired for each mole of VDF formed.)

The process of the present invention allows selectivities of at least up to 90% at conversions of over 20%, even over 30%, or perhaps over 50% to be achieved (selectivity and conversion as defined above). Thus yields of VDF of at least up to 40% are attainable, subject to, amongst other factors, the molar ratio of DCDFM:methane used in the gaseous reactant feed.

The process of the present invention may therefore provide an improved method of preparing VDF from a gaseous reactant mixture which comprises dichlorodifluoromethane, methane and optionally an inert diluent. Surprisingly, by effecting the reaction between methane and DCDFM in a reactor element which contains therein a non-metallic packing material which is stable (i.e. will not decompose or melt) at the elevated reaction temperatures employed, the yield of VDF may be noticeably improved in comparison with known prior art hot tube reactor methods.

The packing material improves the heat transfer properties of the reactor element so that the reaction between the methane and DCDFM takes place in a reaction zone which provides a good rate of heat transfer. Furthermore, certain packing materials may also, it is believed, provide a catalytic effect which will further enhance the productivity of the present process in comparison to known prior art processes.

Suitable packing materials include, for example, carbon, silica, graphite, alumina, or silica alumina, with alumina and particularly graphite being preferred. The packing material may, for example, be in particulate form, or in the form of somewhat larger packing elements. The configuration of such packing elements is normally not critical and such elements may, for example, be cylindrical, spherical or spiral in form, or alternatively disc shaped or irregularly shaped.

In a preferred embodiment the packing material has a high surface area to volume ratio, so that a large surface area of the material is available for contacting with the reactant gases as they pass through the reaction zone. For this reason it may often be preferred to use a particulate packing material, or particularly preferably a packing material having a porous structure.

While the process of the invention requires the use of a reactor element containing a non-metallic packing material, we do not exclude the possibility that the reactor element may also contain a metallic packing material, particularly a metallic catalyst. However the non-metallic packing material should constitute at least 90% and preferably at least 99% of the total packing material contained in the reactor element. Where a metallic packing material is employed it can, for example, be (1) in the form of discrete particles or packing elements embedded in the non-metallic packing material, (2) as a surface coating on a non-metallic support, or (3) as an impregnant located in the interstices of a non-metallic support, providing, of course, that the metallic component is less than 10%, preferably less than 1% of the total.

The quantity of the packing material employed is preferably such that the portion of the reactor element through which the reactant gases pass and in which they react (i.e. the reaction zone) largely comprises the packing material, providing, of course, no substantial resistance, and preferably no resistance, to the flow of reactant gases therethrough is created.

A particularly suitable reactor element for use in the process of the present invention comprises a cylindrical container open at one end for reception of the packing material and having a closed wall portion at the other end, said closed wall portion having holes or ports therein so that a flow of gaseous reactants may enter the reactor element for passage therethrough via the packing material. In effect the reactor element provides a reaction zone which comprises a chamber which contains a suitable packing material. Preferably, the packing material will occupy at least 50% of the total volume of the chamber. A reactor comprising such a reactor element is illustrated in schematic form in FIG. 1.

The reactor element should be constructed out of a thermally conductive material which is stable (stable as hereinbefore defined) at the high operating temperatures of the process. Where inductive heating means are employed it is also a requirement that the material of the reactor element be electrically conducting. Suitable reactor element materials may include, for example, graphite, carbon, certain metals and metal alloys, graphite or carbon being preferred.

Conventional or obvious conveyance means may be used to convey the flow of gas to and from the reactor element; these normally comprise one or more suitably connected ducts of suitable configuration.

The proportion of methane in the gaseous reactant flow entering the reaction zone is preferably at least equivalent to the proportion of DCDFM. However, the gaseous reactant flow may comprise a higher proportion of methane, perhaps as high as 10 moles of methane or even more to 1 of DCDFM. By increasing the proportion of methane relative to the proportion of DCDFM, higher selectivities to VDF at given conversions of DCDFM are attainable, but the use of a substantial excess of methane may be undesirable in view of disposal problems. Preferably, the molar ratio of DCDFM:methane will be in the ratio range 1:1 to 1:10, more preferably in the range 1:1 to 1:5. In general, a substantially equimolar ratio of DCDFM:methane is employed.

The gaseous feed entering the reaction zone may be composed entirely, or substantially entirely, of methane and DCDFM (i.e. the gaseous reactants), or, if desired, it may additionally comprise an inert diluent gas or vapour, which if present is preferably selected from nitrogen, helium or carbon dioxide, with nitrogen being particularly preferred. Steam may also be useful as a diluent in view of its ease of separation. Advantageously, where an inert diluent is used, this may lead to an improvement in the yields of VDF, by further favouring the selective formation thereof. Preferably the proportion of inert diluent (if used) in the gaseous feed entering the reaction zone will not exceed 90%, more preferably it will not exceed 50% of that gaseous feed.

According to a specific embodiment of the present invention high yields of VDF are attainable while using a gaseous reactant feed consisting of a substantially equimolar ratio of DCDFM:methane with little or no inert diluent.

According to the present invention, the process is effected within a temperature range of 500° to 1200° C., more preferably within the range 650° to 950° C. and particularly preferably the temperature employed is within the range 800° to 900° C.

The calculated residence time for the gaseous reactants in the reaction zone is within the range of from 0.1 to 10.0 seconds, preferably 0.5 to 5.0 seconds, and particularly preferably 1.0 to 3.0 seconds. In this specification, the calculated residence time is defined as follows:

Calculated residence time (seconds) at $NTP =$ $$\frac{\text{Reactor element volume}}{\text{Volumetric fluid flow rate}}$$
(ie volume of fluid passing per second)

This residence time is calculated at NTP (normal temperatures and pressures) and is based on the total internal volume of the reactor element when empty (i.e. the volume of the reaction zone without the packing material). It should be understood, that at the high operating temperatures of the process, the calculated residence time will be somewhat longer than the actual residence time. The residence time includes the time taken in the reaction zone for the gaseous reactants to warm up from a low entry temperature (usually about or near ambient) to the high desired temperature imparted by the hot element as well as the time taken for the gaseous reactants to react. It will be appreciated that because the present reaction process employs a packed reactor element which provides good heat transfer characteristics, the warm up period will be extremely short and the gas temperature obtained will be similar to that of the hot reaction zone.

The reaction pressure employed in the process according to the present invention is not normally critical and may be atmospheric, sub-atmospheric, or super-atmospheric. However, operating pressures in the region of atmospheric pressure are preferred, and in general operation at atmospheric pressure, or substantially atmospheric pressure is particularly preferred. It is, therefore, a feature of the present process that good productivities (in terms of VDF yield) are obtainable when the process is operated at or around atmospheric pressure.

The reactor element may be heated by any suitable means, for example, it may be heated by electromagnetic induction, or by means of a furnace suitably disposed around it. Where electromagnetic induction heating is employed as the heating means (as is preferred), this may comprise a primary coil (e.g. of copper tubing)

in an alternating current circuit, with the primary coil surrounding the element (constituting the secondary coil); this is particularly convenient for a cylindrically shaped element wherein the surrounding primary coil will also be cylindrical but of wider diameter. The primary coil will, of course, normally be separated from the element by a reactor casing(s) and/or other structure(s) of the reactor.

When operating the reactor to effect the process of the present invention, the hot exit gas is normally quench cooled on leaving the element to a lower temperature (i.e. below the temperature at which the desired reaction proceeds). Any suitable quench means may be employed. For example, the quench means may comprise a cold inert surface (e.g. the outer surface of a water-cooled body) onto which the exit flow is directed before being conveyed away from the reactor by suitable exit ducting. Alternatively, the quench means may, for example, comprise a flow of inert (to the exit gas) cold fluid (usually gas or vapour although a liquid, e.g. water, could be used). The quench fluid may be directed to sweep over the exit surface of the element, or to meet the hot exit gas just beyond the element, so as to mix with, and hence cool, the hot gas leaving the element. When employing a quenching arrangement of this kind it is preferable to use fluids like steam, nitrogen or carbon dioxide as the quenching agent. Combinations of more than one type of quench means may also be used. Once the hot exit gas from the reactor element has been cooled, it is conveyed away from the reactor element by suitable exit conveyance means.

Accordingly, the process of the present invention may be conveniently carried out using a fluid phase electromagnetic induction heated reactor comprising:

(a) an inductively heatable fluid permeable reactor element which is capable of subjecting the methane and dichlorodifluoromethane reactants to a temperature within the range 500° C. to 1200° C. for a calculated residence time therein within the range of from 0.1 to 10.0 seconds, said reactor element containing a non-metallic packing material therein which is stable at the operating temperatures of the process:

(b) heating means for heating the reactor element by electromagnetic induction;

(c) entry conveyance means for conveying a flow of fluid to be reacted to the entry side of said element for passage therethrough;

(d) exit conveyance means for conveying exit fluid away from the element; and (e) quench means for cooling hot exit fluid from the element.

The exit flow of reacted gas mixture which may include VDF, HCl, unreacted DCDFM and methane, and (if used) diluent, may be handled by conventional techniques (e.g. condensation, freezing, distillation, etc) in order to isolate and collect the VDF.

Figure 1:
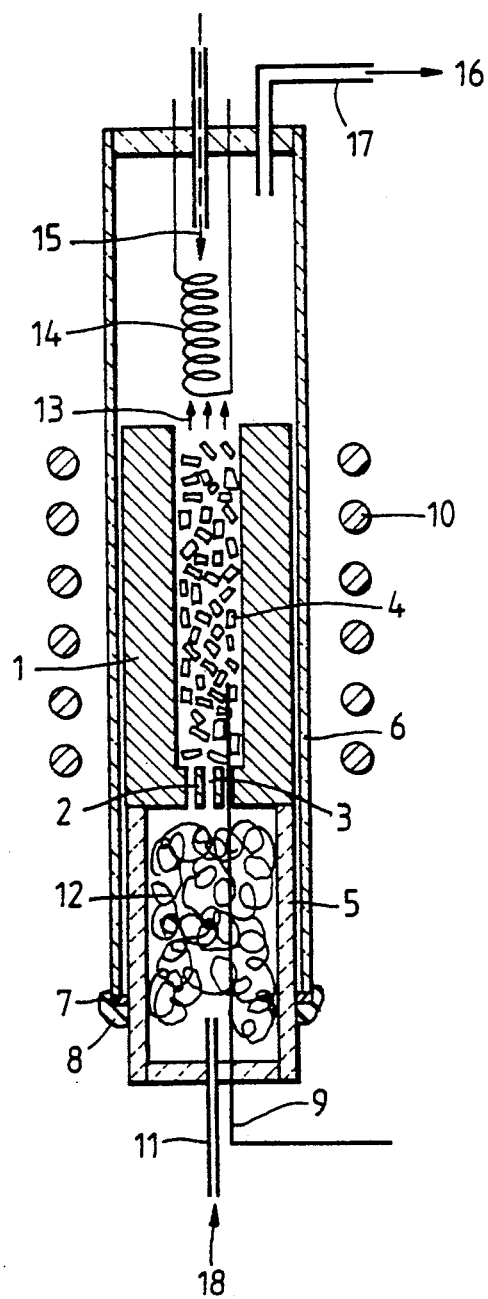
FIG. 1 is a sectional view of one type of induction heated reactor which may be used to carry out the process of the present invention.

In FIG. 1, the reactor comprises a gas-permeable reactor element 1 in the form of a cylindrical container through which the gaseous reactants may pass, said container being open at one end for reception of the packing material, depicted as rectangular sectioned packing elements 4, and having a closed wall portion 2 at the other end, said closed wall portion having holes or ports 3 therein, so that a flow of gaseous reactants may enter the reactor element for passage therethrough via the said packing material.

The gas permeable reactor element is cemented to a machined cylindrical ceramic 5, and surrounded by a reactor casing 6 of a non-conductive material (such as glass or quartz) which is sealed to the ceramic by means of a polytetrafluoroethylene sleeve 7 and a gas-tight silicone rubber seal 8. The reactor element in the drawing is inductively heatable to a temperature of between 500° and 1200° C. (measured by a thermocouple 9) by an electromagnetic induction coil 10 in an alternating current circuit (not shown).

In operation, the gaseous reactants 18 enter the reactor by means of the entrance ducting 11, first passing through the zone within the machined ceramic 5 (which may contain therein some quartz wool 12), and then into the reactor element 1 via the holes 3. As the reactants pass through the reactor element (via the packing elements 4) they are subjected to a temperature with the range 500° to 1200° C. for a calculated residence time therein of between 0.1 and 10.0 seconds. The hot exit fluid 13 which comprises reaction product(s), normally unreacted starting material(s), and, if used, inert diluent is quench cooled on emerging from the reactor element. Any appropriate quench means may be employed, though in FIG. 1 the quench means comprises a water cooled copper coil 14, and a flow of cold nitrogen 15. The cooled exit gas 16 is directed away from the reactor by means of suitably arranged exit ducting 17, whence it is treated by suitable work up means (not shown) to isolate and recover the VDF and other constituents thereof (if required).

The present invention is now illustrated by means of the following examples, which examples are not to be construed as limiting the scope of the present invention.

EXAMPLES 1 AND 2

In both these examples, the reactions were carried out using the reactor shown in FIG. 1 and described in detail above. The reactor element was 7 cms long × 3 cms external diameter × 1 cm internal diameter, was constructed from carbon and contained an alumina packing material occupying about 50% of its internal volume. In Example 1 lumps of a non-porous, low surface area alumina packing material were employed, while in Example 2 a porous, high surface area alumina packing material was used (relative to the packing material used in Example 1). In both examples the calculated residence time for the reactants in the reaction zone was adjusted to 1.0 second.

An equimolar mixture of methane and DCDFM (no inert diluent used) were metered into the reactor using flow controllers, calibrated flow meters and a fixed inlet pressure. The process was operated at about atmospheric pressure and the reactor element was heated by means of electromagnetic induction to a temperature therein of between 800° and 900° C., the temperature being accurately measured by a thermocouple.

After reaction, the gaseous mixture exiting from the reaction zone was quenched by directing a flow of cold nitrogen towards the exit gases, further cooling being effected by means of a water cooled copper coil.

After quenching, the exit gases were passed through a scrubber in order to remove any acidic components, dried, and then analysed by means of a calibrated gas chromatograph. Analysis was effected on the exit gases resulting from the operation of the process over a range of temperatures between 800° and 900° C. Higher temperatures (i.e. towards the upper limit of this range) tended to facilitate better conversion of the DCDFM, while leading to a reduction in the selectivity of VDF formation (conversion and selectivity as hereinbefore defined).

Figure 2:
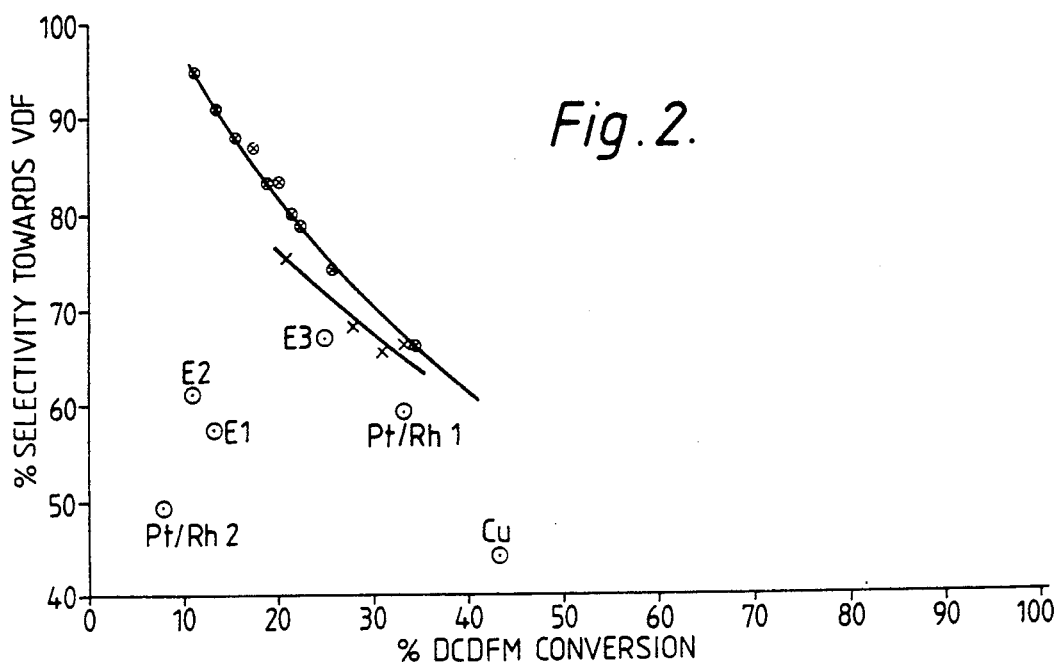
FIG. 2 is a graph showing the selectivity towards VDF formation as a function of DCDFM conversion for the reaction between an equimolar mixture of DCDFM and methane carried out according to the process of the present invention using the induction heated reactor shown in FIG. 1 in which the reactor element contained an alumina packing material therein.

The results are illustrated graphically in FIG. 2, with the results obtained from Example 1 being denoted by crosses, and the results from Example 2 by crosses enclosed in circles. Also marked on FIG. 1 are the results exemplified in U.S. Pat. No. 2,687,440, which passes a mixture of DCDFM and methane through the hot reaction zone provided by a furnace heated hot tube, which may optionally comprise therein a metallic catalyst. The results exemplified in U.S. Pat. No. 2,687,440 are not specified therein in terms of the conversion of DCDFM and the selectivity to VDF formation, but, in fact, specify the percentage of DCDFM and products formed therefrom (including VDF) which are present in the exit gases emerging from the reactor. However, by applying the principle that the DCDFM which reacted formed only those products that were detectable in the exit gases, and that no carbon, high molecular weight halocarbons or halohydrocarbons remained in the reactor element, we have estimated what amounts to an optimum selectivity and conversion for the process described in U.S. Pat. No. 2,687,440. The reaction conditions and results relating to these prior art hot tube reactor examples are listed in Table 1. It is evident from FIG. 2 that increasing the surface area of the alumina packing material provides for an improvement in the selectivity/conversion characteristics (i.e. a higher selectivity at a given conversion). Whether using a high or low surface area alumina packing material superior results are obtainable over the prior art hot tube reactor methods.

EXAMPLES 3 AND 4

The basic method and apparatus used were as described in Examples 1 and 2, except that a graphite packing material was used. The graphite packing material occupied about 50% of the total internal volume of the reactor element. For Example 3, lumps of a non-porous, low surface area graphite packing material were employed, while in Example 4 a porous, high surface area graphite packing material was used (relative to the packing material used in Example 3). For both Examples 3 and 4, the calculated residence time for the fluid reactants in the reaction zone was adjusted to 1.0 second.

Figure 3:
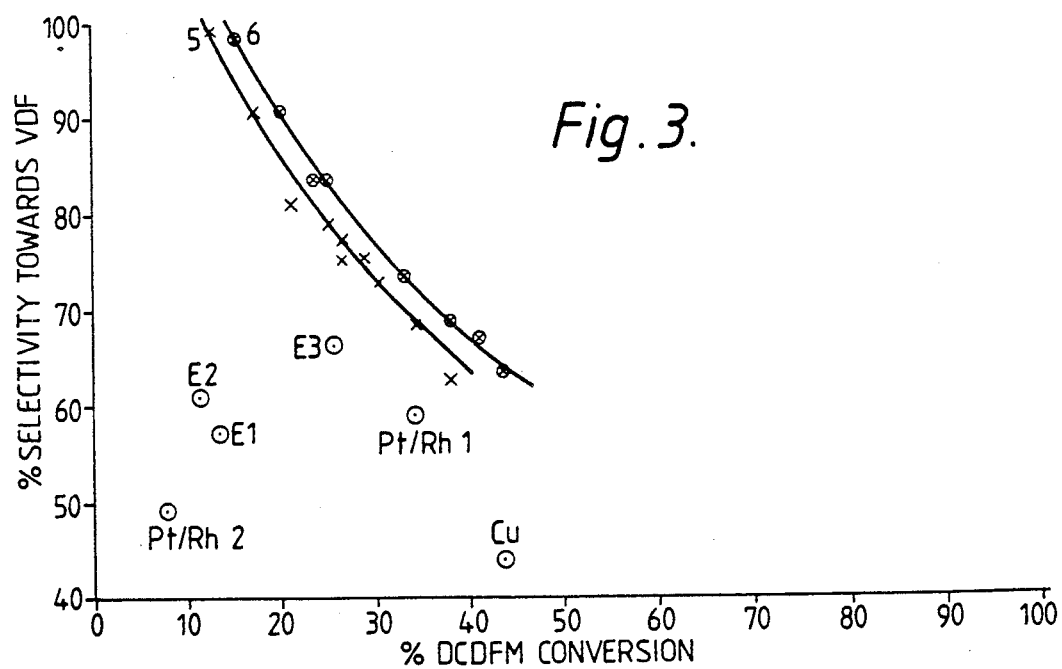
FIG. 3 is a graph showing the selectivity towards VDF formation as a function of DCDFM conversion for the reaction between an equimolar mixture of DCDFM and methane carried out according to the process of the present invention using the induction heated reactor shown in FIG. 1 in which the reactor element contained a graphite packing material therein.

The results are illustrated graphically in FIG. 3, with the results obtained from Example 3 being denoted by crosses, and the results from Example 4 by crosses enclosed in circles. Also marked, for comparison purposes only, are the prior art hot tube reactor results shown in Table 1.

It is evident from FIG. 3, that increasing the surface area of the graphite packing material provides for an improvement in the selectivity/conversion characteristics (i.e. a higher selectivity at a given conversion). Whether using a high or a low surface area graphite packing material superior results are obtainable over the prior art hot tube reactor methods.

EXAMPLE 5

The basic method and apparatus used were as described in Examples 1 and 2, except that a high surface area porous carbon packing material was used. The porous carbon packing material occupied about 50% of the total internal volume of the reactor element. The calculated residence time for the fluid reactants in the reaction zone was adjusted to 1.0 second.

Figure 4:
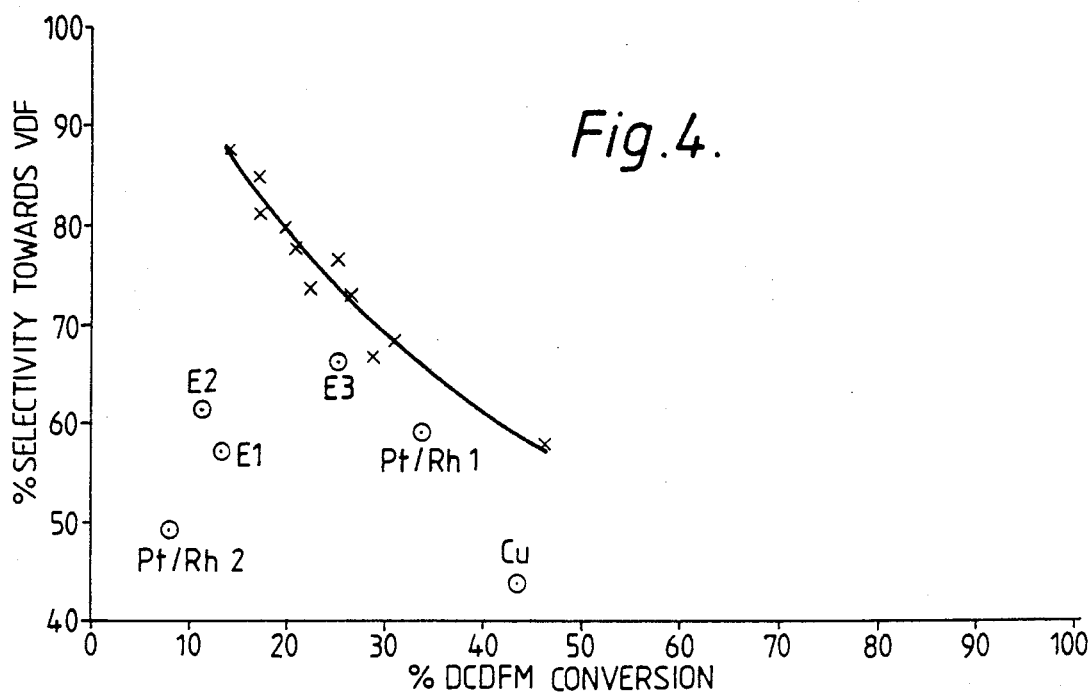
FIG. 4 is a graph showing the selectivity towards VDF formation as a function of DCDFM conversion for the reaction between an equimolar mixture of DCDFM and methane carried out according to the process of the present invention using the induction heated reactor shown in FIG. 1 in which the reactor element contained a porous carbon packing material therein.

The results are illustrated graphically in FIG. 4 which also has marked thereon, for comparison purposes, the prior art hot tube reactor results shown in Table 1. It is evident from FIG. 4, that the process of the present invention is capable of providing superior results, in terms of a higher selectivity at a given conversion, over the prior art hot tube reactor methods.

EXAMPLE 6

This comparative example demonstrates the affect of reducing the molar ratio of DCDFM in the gaseous reactant feed.

The basic method and apparatus used were as described in Examples 1 and 2, except that the gaseous reactant feed comprised a 1:3 mixture of DCDFM:methane (no inert diluent was used). A high surface area graphite packing material was employed, and the calculated residence time for the fluid reactants in the reaction zone was adjusted to 1.0 second.

Figure 5:
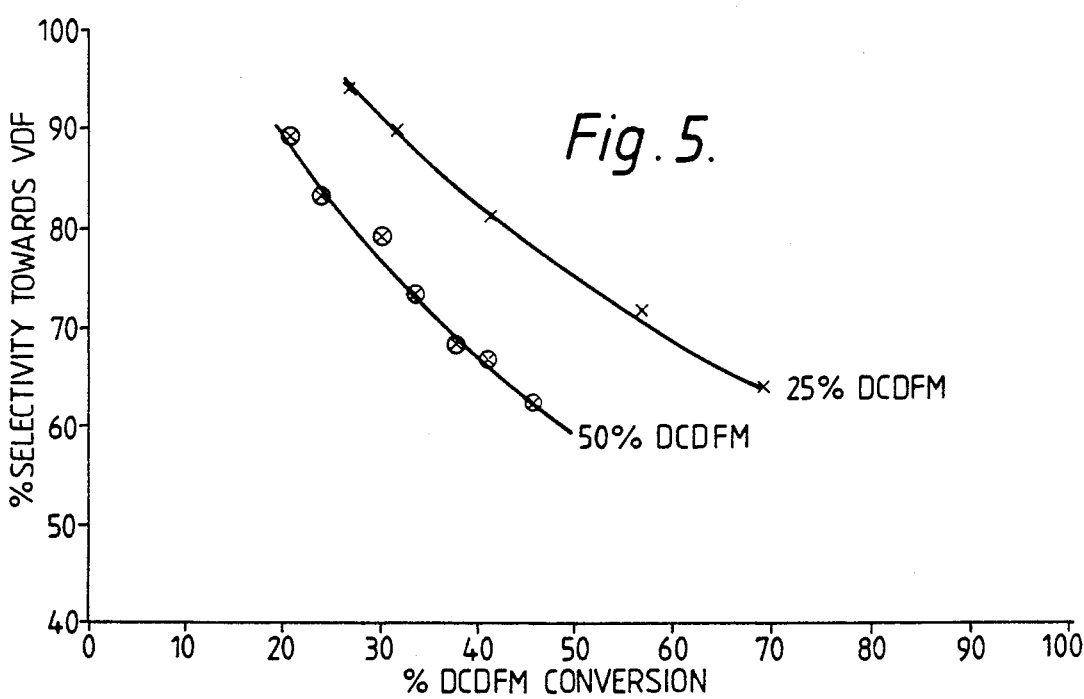
FIG. 5 is a graph showing the selectivity towards VDF formation as a function of DCDFM conversion for the reaction between a 1:2 mixture of DCDFM:methane carried out according to the process of the present invention using the induction heated reactor shown in FIG. 1 in which the reactor element contained a graphite packing material therein.

The results are illustrated graphically in FIG. 5 (denoted by crosses), which also has marked thereon, for comparison purposes, the results obtained from Example 4 (denoted by crosses enclosed in circles). It is evident from FIG. 5, that by increasing the molar proportion of methane in the gaseous reactant feed improved selectivities towards VDF formation are obtainable, so that a higher selectivity at a given conversion may be achieved.

TABLE 1

| GRAPHICAL CODE | TEMPERATURE OF REACTION (°C.) | RATIO OF DCDFM:METHANE REACTANTS | RESIDENCE TIME (SECONDS) | CONVERSION OF DCDFM (%) | CALCULATED SELECTIVITY OF VDF FORMATION (%) |
| --- | --- | --- | --- | --- | --- |
| E1 | 720–760 | 1:1 | 6.4 | 12.9 | 57.4 |
| E2 | 720–760 | 1:1 | 3.8 | 11.0 | 61.3 |
| E3 | 770–810 | 6:5 | 2.7 | 24.9 | 66.3 |
| Pt/Rh 1 | 770–810 | 6:5 | 2.7 | 33.7 | 59.05 |
| Pt/Rh 2 | 720–760 | 3:2 | 3.0 | 7.1 | 49.4 |
| Cu | 720–760 | 6:5 | 2.7 | 43.1 | 44.4 |

E = empty tube.
Pt/Rh = platinum/rhodium alloy catalyst used.
Cu = copper catalyst used.

I claim:

1. Process for preparing vinylidene fluoride from the reaction of dichlorodifluoromethane with methane which process comprises passing a gaseous flow of methane and dichlorodifluoromethane through a heated reaction zone containing a non-metallic packing material which is stable at the operating temperatures of the process and which subjects the gaseous reactants to a temperature with the range 500° C. to 1200° C. and maintaining the gaseous flow so that the calculated residence time for the gaseous reactants in the reaction zone is within the range of from 0.1 to 10.0 seconds.

2. Process according to claim 1 wherein the packing material is alumina.

3. Process according to claim 1 wherein the packing material is graphite.

4. Process according to claim 1 wherein the packing material has a porous structure.

5. Process according to claim 1 wherein the reaction zone subjects the gaseous reactants to a temperature within the range 650° C. to 950° C.

6. Process according to claim 5 wherein the reaction zone subjects the gaseous reactants to a temperature within the range 800° C. to 900° C.

7. Process according to claim 1 wherein the calculated residence time is within the range of from 0.5 to 5.0 seconds.

8. Process according to claim 7 wherein the calculated residence time is within the range of from 1.0 to 3.0 seconds.

9. Process according to claim 1 wherein the reaction zone additionally contains a metallic packing material in an amount of up to 10% by weight based on the total weight of the non-metallic and metallic packing material.

10. Process according to claim 9 wherein the metallic packing material is present in an amount of up to 1% by weight based on the total weight of the non-metallic and metallic packing material.

11. Process according to claim 1 wherein the molar ratio of dichlorodifluoromethane:methane in the gaseous flow entering the reaction zone is within the ratio range 1:1 to 1:10.

12. Process according to claim 11 wherein the molar ratio of dichlorodifluoromethane:methane is within the ratio range 1:1 to 1:5.

13. Process according to claim 12 wherein the molar ratio of dichlorodifluoromethane:methane is substantially equimolar.

14. Process according to claim 1 wherein the gaseous flow of methane and dichlorodifluoromethane entering the reaction zone includes a gaseous or vapourous diluent.

15. Process according to claim 1 when carried out at substantially atmospheric pressure.

16. Process according to claim 1 wherein said reactor element is inductively heated.

* * * * *